United States Patent
Tokunaga

(10) Patent No.: US 11,273,085 B2
(45) Date of Patent: Mar. 15, 2022

(54) ABSORBENT ARTICLE

(71) Applicant: DAIO PAPER CORPORATION, Ehime (JP)

(72) Inventor: Sachiko Tokunaga, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 656 days.

(21) Appl. No.: 16/302,172

(22) PCT Filed: Jun. 12, 2017

(86) PCT No.: PCT/JP2017/021591
§ 371 (c)(1),
(2) Date: Nov. 16, 2018

(87) PCT Pub. No.: WO2017/217355
PCT Pub. Date: Dec. 21, 2017

(65) Prior Publication Data
US 2019/0159945 A1 May 30, 2019

(30) Foreign Application Priority Data
Jun. 14, 2016 (JP) .............................. JP2016-118077

(51) Int. Cl.
*A61F 13/15* (2006.01)
*A61F 13/533* (2006.01)
(Continued)

(52) U.S. Cl.
CPC ........ *A61F 13/533* (2013.01); *A61F 13/4753* (2013.01); *A61F 13/532* (2013.01);
(Continued)

(58) Field of Classification Search
CPC .. A61F 13/533; A61F 13/4753; A61F 13/532; A61F 13/2088; A61F 13/4752; A61F 13/4704; A61F 13/47218
(Continued)

(56) References Cited

U.S. PATENT DOCUMENTS

2006/0276767 A1 12/2006 Ueminami et al.
2010/0178456 A1* 7/2010 Kuroda .................... B32B 7/04
428/136
(Continued)

FOREIGN PATENT DOCUMENTS

| EP | 2260808 | 12/2010 |
| EP | 2409673 | 1/2012 |

(Continued)

OTHER PUBLICATIONS

International Search Report for PCT/JP2017/021591 dated Aug. 8, 2017.
(Continued)

*Primary Examiner* — Jacqueline F Stephens
(74) *Attorney, Agent, or Firm* — IPUSA, PLLC

(57) ABSTRACT

The present invention prevents an absorbent body from twisting and splitting while maintaining the capability of fitting onto the buttocks of a wearer even when the absorbent body has a low fabric weight. The absorbent body (4) has a large number of compressed parts (20, 20, . . . ) formed in a region other than a region that extends in a widthwise center section along the longitudinal direction and includes portions corresponding to a body fluid excretion part (H) and the intergluteal cleft of the wearer. A region including a portion corresponding to the intergluteal cleft is an easily deformable region (21) without compressed parts (20). The easily deformable region (21) extends to an intermediate position in the longitudinal direction and does not reach the (Continued)

rear end of the absorbent body (4). The region extending behind the easily deformable region (21) to the rear end of the absorbent body (4) has compressed parts (20) formed thereon.

5 Claims, 5 Drawing Sheets

(51) Int. Cl.
    *A61F 13/534*    (2006.01)
    *A61F 13/532*    (2006.01)
    *A61F 13/475*    (2006.01)
    *A61F 13/20*     (2006.01)
    *A61F 13/47*     (2006.01)
    *A61F 13/472*    (2006.01)

(52) U.S. Cl.
    CPC ........ *A61F 13/534* (2013.01); *A61F 13/2088* (2013.01); *A61F 13/4704* (2013.01); *A61F 13/47218* (2013.01)

(58) Field of Classification Search
    USPC .......................... 604/378, 379, 380, 385.101
    See application file for complete search history.

(56) References Cited

U.S. PATENT DOCUMENTS

2011/0319851 A1* 12/2011 Kudo ................. A61F 13/4756
                                                                                        604/380
2013/0165885 A1*  6/2013 Kurihara ............... A61F 13/538
                                                                                        604/380

FOREIGN PATENT DOCUMENTS

| JP | 2004-016373 | 1/2004 |
| --- | --- | --- |
| JP | 2008-136738 | 6/2008 |
| JP | 2011-120764 | 6/2011 |
| JP | 2013-248309 | 12/2013 |
| JP | 2013-255551 | 12/2013 |
| JP | 2014-068745 | 4/2014 |
| WO | 98/27904 | 7/1998 |
| WO | 2012/090830 | 7/2012 |
| WO | 2014/119601 | 8/2014 |

OTHER PUBLICATIONS

Extended European Search Report for 17813251.0 dated Feb. 28, 2019.

* cited by examiner

ABSORBENT ARTICLE

TECHNICAL FIELD

The present invention relates to an absorbent article used mainly for sanitary napkins, pantyliners, incontinence pads, toiletries, etc., and specifically, to an absorbent article in which multiple compressed parts are formed in a predetermined region of an absorbent body.

BACKGROUND ART

Conventionally, as absorbent articles such as pantyliners, sanitary napkins, and incontinence pads, etc., there are known articles in which an absorbent body made of cotton-like pulp, etc., is interposed between a liquid impermeable back sheet such as a polyethylene sheet or a polyethylene sheet laminated non-woven fabric, and a liquid permeable surface sheet such as a non-woven fabric or a liquid permeable plastic sheet.

Many improvements have been made to these types of absorbent articles. Specifically, various kinds of these absorbent articles having a structure capable of efficiently absorbing body fluids, etc., according to the posture state of the wearer during the wearing time range such as the bedtime time range and the wake-up time range, have been proposed. Among these, in so-called night absorbent articles to be worn during bedtime, a structure to prevent rear leakage by relatively increasing the area of the absorbent body covering a region ranging from the body fluid excretion part to the hip side of the wearer, is often adopted.

As such a night absorbent article, many absorbent articles having an absorbent body with an increased thickness, in order to secure the absorption amount, have been commercially available. However, in recent years, it has been pointed out that the cause of the transmission leakage of body fluid while the wearer is in a sleeping posture, is that the skin surface and the absorbent article do not come into close contact with each other, and, therefore, a gap is formed between the skin surface and the absorbent article, and the body fluid is transmitted along the intergluteal cleft and leaks outside. Thus, even in the case of a night absorbent article, there is a tendency of placing importance on the capability of fitting onto the wearer's body. In accordance with such needs, there is a tendency to make the absorbent body thinner (reduce the fabric weight) in order to suppress the sense of roughness at the time of wearing the absorbent article.

For example, the following patent literature 1 discloses an absorbent article in which a portion requiring absorption/diffusion of body fluid in the vicinity of the center (crotch portion) of the absorbent body is densely embossed, and the front and rear portions thereof are sparsely embossed with an increased embossing pitch in the longitudinal direction of the absorbent body, so that the entire embossment forms a continuous pattern.

Furthermore, the following patent literature 2 discloses an absorbent article in which surface embossing applied to the liquid pervious surface sheet from the surface side of the liquid pervious surface sheet, and core embossing is applied to the absorbent body from the surface side of the absorbent body in a region that does not overlap with the surface embossing. By the surface embossing, a section where large-area surface embossing forming relatively large embossing areas is applied, and a section where small-area surface embossing forming relatively small embossing areas is applied, are alternately formed. By the core embossing, a section where at least the aforementioned small-area surface embossing is applied, is formed.

CITATION LIST

Patent Literature

[PTL 1]
Japanese Unexamined Patent Application Publication No. 2004-16373
[PTL 2]
Japanese Unexamined Patent Application Publication No. 2013-248309

SUMMARY OF INVENTION

Technical Problem

However, in the absorbent articles disclosed in the above-mentioned patent literature 1 and 2, compressed parts are applied also to the portions corresponding to the body fluid excretion part and the intergluteal cleft, and, therefore, there is a possibility that the absorbent body becomes hard and the wearing feeling is degraded. On the other hand, when the thickness of the absorbent body is reduced by reducing the fabric weight, the rigidity (elasticity) of the absorbent body is weakened, so that there has been a problem that the absorbent body is largely twisted or the absorbent body is split, due to the movement of the wearer's body such as rolling over in bed. The twisting and splitting of the absorbent body not only degrades the wearing feeling, but also particularly degrades the capability of fitting onto the buttocks, thereby causing rear leakage.

It is therefore a primary object of the present invention to provide an absorbent article that can prevent twisting and splitting of an absorbent body while maintaining the capability of fitting onto the buttocks even if the absorbent body has a low fabric weight.

Solution to Problem

In order to solve the above problem, the present invention according to claim 1 provides an absorbent article in which an absorbent body is interposed between a liquid permeable surface sheet and a liquid impermeable back sheet, wherein in the absorbent body, multiple compressed parts are formed in a region other than a region that is a widthwise center portion extending along a longitudinal direction, the region that is the widthwise center portion including a portion corresponding to a body fluid excretion part of a wearer and a portion corresponding to an intergluteal cleft of the wearer, and a region including the portion corresponding to the intergluteal cleft is an easily deformable region where the compressed parts are not formed.

In the present invention according to claim 1, by forming multiple compressed parts in a region other than a predetermined region of the absorbent body, the rigidity of the absorbent body in the region where the compressed parts are formed is increased, and, therefore, even if the absorbent body has a low fabric weight, it will be possible to prevent twisting and splitting of the absorbent body due to movements of the body at the time of wearing the absorbent article. On the other hand, the region including the portion corresponding to the intergluteal cleft of the wearer is an easily deformable region in which the compressed parts are not formed, and, therefore, the easily deformable region deforms by protruding toward the skin side in the longitudinal direction along the intergluteal cleft when the absorbent article is worn, and it is possible to maintain the capability of fitting onto the buttocks.

The present invention according to claim 2 provides the absorbent article according to claim 1, wherein the easily deformable region extends to an intermediate position in the longitudinal direction of the absorbent body and does not reach a rear end of the absorbent body, and the compressed parts are formed in a range extending behind the easily deformable region to the rear end of the absorbent body.

In the present invention according to claim 2, the easily deformable region is formed up to the intermediate position in the longitudinal direction without reaching the rear end of the absorbent body, and the compressed parts are formed in a range extending behind the easily deformable region to the rear end of the absorbent body, and, therefore, it is possible to prevent the absorbent body from twisting and splitting in the region behind the easily deformable region, and there is the region having high rigidity due to the compressed parts at the rear end of the easily deformable region, so that it is possible to prevent twisting and splitting of the absorbent body in the easily deformable region in the intermediate position.

The present invention according to claim 3 provides the absorbent article according to claim 1 or 2, wherein a ratio of an area occupied by the compressed parts per unit area of the absorbent body is higher for the compressed parts that are formed in regions on both sides of the portion corresponding to the body fluid excretion part, than for the compressed parts that are formed in a region on a front side of and in a region on a rear side of the portion corresponding to the body fluid excretion part.

In the present invention according to claim 3, the ratio of an area occupied by the compressed parts per unit area of the absorbent body is higher for the compressed parts that are formed in regions on both sides of the portion corresponding to the body fluid excretion part, than for the compressed parts that are formed in a region on a front side of and in a region on a rear side of the portion corresponding to the body fluid excretion part, and, therefore, it is possible to relatively increase the rigidity of both side regions of the portion corresponding to the body fluid excretion part that is liable to receive pressure from the inner part of the roots of the legs at the time of wearing the absorbent article, and it is possible to reliably prevent twisting and splitting of the absorbent body in this region.

The present invention according to claim 4 provides the absorbent article according to any one of claims 1 to 3, wherein the compressed parts are formed in a compressed part pattern forming a substantially rhombic grid, in which a pattern, in which oval compressed parts are disposed adjacent to each other in a cross direction centering around a dot-like compressed part, is repeated, and the dot-like compressed part is disposed at a center of each mesh of the rhombic grid.

In the present invention according to claim 4, as an optimum compressed part pattern for increasing the rigidity of the absorbent body, dot-like compressed parts and oval compressed parts are disposed to form a substantially rhombic grid, and a dot-like compressed part is disposed at the center of each mesh of the rhombic grid. By disposing the compressed parts in such a compressed part pattern, the restoring force of the absorbent body after the compressing process is appropriately suppressed, without impairing the cushioning property and the body fluid holding performance of the absorbent body, and the rigidity of the absorbent body can be reliably increased by providing the compressed parts.

Furthermore, by disposing the dot-like compressed parts and the oval compressed parts in a substantially rhombic grid pattern, the leg pressure from the outside in the width direction can be received while the leg pressure is distributed in the longitudinal direction by the inclined oval compressed parts, and it is possible to more reliably prevent twisting and splitting of the absorbent body caused by the concentration of pressure in a specific direction.

The present invention according to claim 5 provides the absorbent article according to claim 4, wherein the dot-like compressed part, which is formed in a region on a front side of and in a region on a rear side of the portion corresponding to the body fluid excretion part, is formed such that a length in the longitudinal direction of the absorbent article and a length in a width direction of the absorbent article are substantially a same length, and the dot-like compressed part, which is formed in regions on both sides of the portion corresponding to the body fluid excretion part, is formed so as to have a shape elongated in the longitudinal direction of the absorbent article, and to have a relatively larger area than the dot-like compressed part formed in the region on the front side of and in the region on the rear side of the portion corresponding to the body fluid excretion part.

In the present invention according to claim 5, in the case where dot-like compressed parts and oval compressed parts are disposed in a compressed portion pattern, the shapes of the dot-like compressed parts are different between the front region and the rear region of the portion corresponding to the body fluid excretion part, and the regions on both sides of the body fluid excretion part. Specifically, the dot-like compressed part, which is formed in a region on a front side of and in a region on a rear side of the portion corresponding to the body fluid excretion part, is formed to have a shape such as a circle such that a length in the longitudinal direction of the absorbent article and a length in a width direction of the absorbent article are substantially a same length, and the dot-like compressed part, which is formed in regions on both sides of the portion corresponding to the body fluid excretion part, is formed so as to have a shape elongated in the longitudinal direction of the absorbent article, and to have a relatively larger area than the dot-like compressed part formed in the region on the front side of and in the region on the rear side of the portion corresponding to the body fluid excretion part. Therefore, in both side regions of the portion corresponding to the body fluid excretion part, the increase in rigidity of the absorbent body by the compression parts becomes more notable, and it is possible to reliably prevent twisting and splitting of the absorbent body caused by the leg pressure from the outside in the width direction. Furthermore, in both side regions of the portion corresponding to the body fluid excretion part, the dot-like compressed part is formed in a shape elongated in the longitudinal direction of the absorbent article, and, therefore, it is possible to form a line having high rigidity along the longitudinal direction of the absorbent article formed by the dot-like compressed parts, and the resistance force against the leg pressure from the outside in the width direction can be increased.

The present invention according to claim 6 provides the absorbent article according to any one of claims 1 to 5, wherein a middle-high portion is provided in the absorbent body, the middle-high portion being formed by increasing a thickness of the absorbent body toward a skin side in the region including the portion corresponding to the body fluid excretion part.

In the present invention according to claim 6, the middle-high portion of the absorbent body is provided in the region including the portion corresponding to the body fluid excretion part, and, therefore, the adhesion with the body fluid excretion part is further improved, and the amount of the body fluid transmitting along the body can be largely reduced.

Advantageous Effects of Invention

As described in detail above, according to the present invention, even when the absorbent body has a low fabric weight, it is possible to prevent the absorbing body from twisting and splitting while maintaining the capability of fitting onto the buttocks.

DESCRIPTION OF EMBODIMENTS

Figure 1:
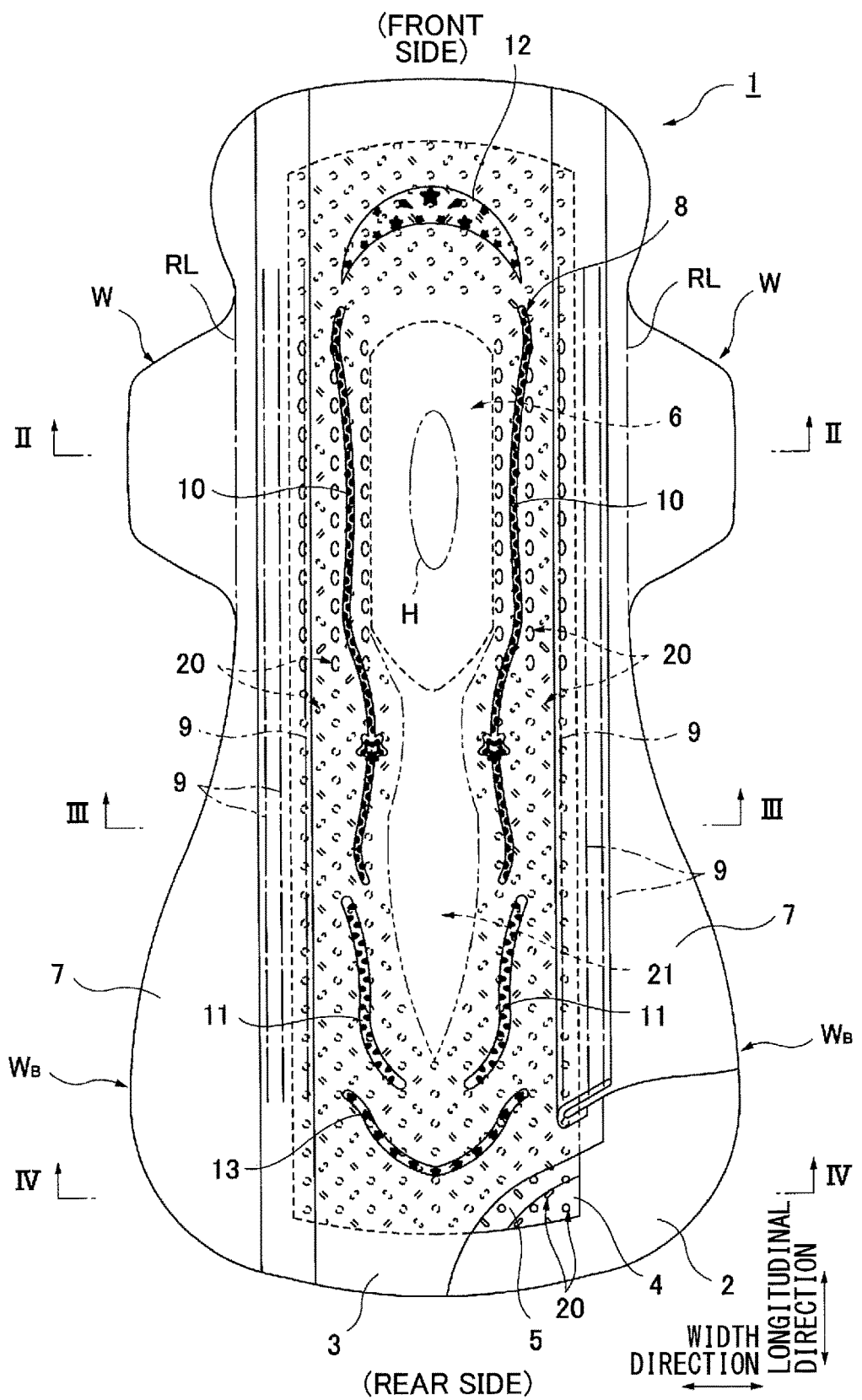
FIG. 1 is a partial cutaway development view of a sanitary napkin 1 according to the present invention.

Hereinafter, embodiments of the present invention will be described in detail with reference to the drawings.
[Basic Structure of Sanitary Napkin 1]
As illustrated in FIGS. 1 to 4, a sanitary napkin 1 according to the present invention includes a liquid impermeable back sheet 2 formed of a polyethylene sheet, etc., a liquid permeable surface sheet 3 for quickly permeating menstrual blood and vaginal discharge, etc. (hereinafter collectively referred to as "body fluid"), an absorbent body 4 formed of cotton-like pulp or synthetic pulp interposed between these sheets 2 and 3, and a side non-woven fabric 7 provided on both side portions of the skin contact surface side across substantially the entire length along the longitudinal direction. Around the absorbent body 4, at the upper and lower edge portions thereof, the outer edge portions of the liquid impermeable back sheet 2 and the liquid permeable surface sheet 3 are joined by a joining means such as an adhesive such as hot melt, a heat seal, and an ultrasonic seal, etc., and at both side edge portions around the absorbent body 4, the liquid impermeable back sheet 2 extended sideways beyond the absorbent body 4 and the side non-woven fabric 7 are joined by a joining means such as an adhesive such as hot melt, a heat seal, and an ultrasonic seal, etc., and, therefore, a flap portion where the absorbent body does not intervene, is formed. Note that in the illustrated example, in order to maintain the shape of the absorbent body 4 and to improve the diffusibility of the absorbent body 4, the absorbent body 4 is surrounded by an encapsulating sheet 5 formed of crepe paper or non-woven fabric, etc.; however, the encapsulating sheet 5 is not required to be provided. Furthermore, although not illustrated, a second sheet, which is formed of a hydrophobic non-woven fabric, having substantially the same shape as the liquid permeable surface sheet 3, may be disposed adjacent to the non-skin side of the liquid permeable surface sheet 3.

Hereinafter, the structure of the sanitary napkin 1 will be described in detail. As the liquid impermeable back sheet 2, a sheet material that has at least a water-impermeable property, such as polyethylene, etc., is used; however, from the viewpoint of preventing steaming, it is desirable to use a material having moisture permeability. As this water-impermeable/moisture-permeable sheet material, a microporous sheet obtained by melt-kneading an inorganic filler in an olefin-based resin such as polyethylene or polypropylene, etc., for molding a sheet and then stretching the sheet in a uniaxial direction or biaxial direction, is suitably used. One or a plurality of adhesive layers (not illustrated) are formed along the longitudinal direction of the napkin on the non-skin side surface (outer surface) of the liquid impermeable back sheet 2, so as to fix the sanitary napkin 1 to underwear when the sanitary napkin 1 is worn on the body. As the liquid impermeable back sheet 2, a poly-laminate non-woven fabric in which a plastic film and a non-woven fabric are laminated, may be used.

Next, as the liquid permeable surface sheet 3, a porous or nonporous nonwoven fabric, or a porous plastic sheet, etc., is suitably used. As the material fiber forming the non-woven fabric, in addition to synthetic fiber such as olefin-based, polyester-based, and polyamide-based fiber, etc., such as polyethylene or polypropylene, etc., regenerated fiber such as rayon or cupra, etc., and natural fiber such as cotton, may be used. The non-woven fabric may be obtained by appropriate processing methods such as a spun lace method, a spun bond method, a thermal bonding method, a melt blown method, and a needle punching method, etc. Among these processing methods, the spun lace method is excellent in terms of flexibility and drapability, and the thermal bonding method is excellent in terms of bulkiness and having high compression recovery properties. When multiple through holes are formed in the liquid permeable surface sheet 3, the body fluid is quickly absorbed, and the dry touch property is excellent. The fiber of the non-woven fabric may be either of long fiber or short fiber; however, short fiber is preferably used for giving the texture of toweling. Furthermore, in order to facilitate the embossing treatment, it is preferable to use an olefin-based fiber such as polyethylene or polypropylene having a relatively low melting point. It is also possible to suitably use composite fiber such as core-sheath type fiber having a core made of fiber with a high melting point and a sheath made of fiber with a low melting point, side-by-side type fiber, and splittable fiber.

The absorbent body 4 interposed between the liquid impermeable back sheet 2 and the liquid permeable surface sheet 3 is formed of, for example, cotton-like pulp and a water-absorbent polymer. The water-absorbent polymer is mixed, for example, as granular powder, in the pulp constituting the absorbent body. Examples of the pulp include cellulose fiber such as chemical pulp and dissolved pulp obtained from wood, and artificial cellulose fiber such as rayon and acetate, etc., and softwood pulp having a longer fiber length than hardwood pulp is suitably used in terms of function and price. The fabric weight (fabric weight) of the absorbent body 4 is preferably 290 $g/m^2$ to 420 $g/m^2$, and more preferably 350 $g/m^2$ to 390 $g/m^2$.

Furthermore, synthetic fiber may be mixed in the absorbent body 4. As the synthetic fiber, polyolefin-based fiber such as polyethylene or polypropylene, etc., polyester-based fiber such as polyethylene terephthalate and polybutylene terephthalate, etc., polyamide-based fiber such as nylon, or copolymers thereof, etc., may be used, or a mixture of two types of these fibers may be used. Furthermore, composite fiber such as core-sheath type fiber having a core made of fiber with a high melting point and a sheath made of fiber with a low melting point, side-by-side type fiber, and splittable fiber, may be used. With respect to synthetic fiber, in the case of hydrophobic fiber, it is desirable to use a fiber that is surface-treated with a hydrophilizing agent so as to have hydrophilicity for body fluids.

Figure 2:
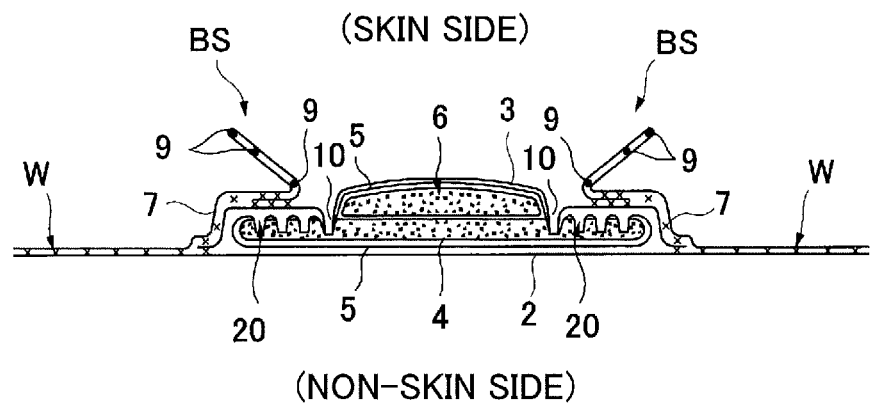
FIG. 2 is a view taken along an arrow line II-II of FIG. 1.

As illustrated in FIGS. 1 and 2, it is preferable to provide a middle-high portion 6 of the absorbent body thickening towards the skin side in a region, including a portion corresponding to a body fluid excretion part H, of the absorbent body 4. The middle-high portion 6 is at the skin side surface of the absorbent body 4, and is disposed at the center in the width direction of the absorbent body 4, and is formed to be smaller in the width dimension and the longitudinal dimension relative to the absorbent body 4. If the fabric weight of the middle-high portion 6 is too high, the rigidity increases and the adhesion to the body decreases, whereas if the fabric weight of the middle-high portion 6 is too low, the adhesion with the body fluid excretion part H decreases, and, therefore, the fabric weight of the middle-high portion 6 is to be 450 g/m$^2$ to 750 g/m$^2$, particularly 600 g/m$^2$ to 640 g/m$^2$.

The middle-high portion 6 is formed in a vertically elongated substantially oblong shape long in the longitudinal direction of the napkin, in a region including the body fluid excretion part H of the wearer. It is preferable that the middle-high portion 6 be disposed only in a region including a portion corresponding to the body fluid excretion part H and not in a region including a portion corresponding to the intergluteal cleft on the rear side. The region including the portion corresponding to the intergluteal cleft is an easily deformable region 21 as described later in detail.

Compressed grooves 8 recessed from the outer surface side of the liquid permeable surface sheet 3 toward the liquid impermeable back sheet 2, may be formed at least on both sides of the middle-high portion 6 at respective positions near and outside the middle-high portion 6. The compressed groove 8 is preferably formed on both side portions of at least a region corresponding to the body fluid excretion part H. Specifically, in the example illustrated in FIG. 1, on both side portions from a region including a portion corresponding to the body fluid excretion part H to a region including the portion corresponding to the intergluteal cleft, the compressed grooves 8 are formed of front side longitudinal compressed grooves 10, 10 continuously formed along the substantially longitudinal direction of the sanitary napkin 1, rear side longitudinal compressed grooves 11, 11 that are disposed on the rear side of and spaced apart from the front side longitudinal compressed grooves 10, 10 and that are continuously formed along substantially the longitudinal direction of the sanitary napkin 1 at both sides of the portion corresponding to the rear end portions of the intergluteal cleft, a front end crescent shaped compressed groove 12 that is disposed in front of and spaced apart from the front side longitudinal compressed grooves 10, 10 and that is formed in a crescent shape substantially along the width direction of the sanitary napkin 1 and that crosses the longitudinal center line of the sanitary napkin 1 in the width direction, and a rear end curved shaped compressed groove 13 that is disposed on the rear side of and spaced apart from the rear side longitudinal compressed grooves 11, 11 and that is formed in a curved shape that bulges toward the rear and that crosses the longitudinal center line of the sanitary napkin 1 in the width direction. The compressed groove 8 is formed by integrally compressing a portion from the liquid permeable surface sheet 3 to the absorbent body 4, by thermal embossment from the outer surface side of the liquid permeable surface sheet 3.

The middle-high portion 6 contains at least pulp fiber and synthetic fiber, and the ratio of the mixture of pulp fiber: synthetic fiber is to be 80 to 20:20 to 80, preferably 40 to 60:60 to 40 in terms of weight. Furthermore, the middle-high portion 6 may contain a water-absorbent polymer. Examples of the water-absorbent polymer include polyacrylate crosslinked products, self-crosslinked polyacrylic acid salts, saponified products of acrylic acid ester-vinyl acetate copolymer crosslinked products, crosslinked isobutylene/maleic anhydride copolymers, polysulfone acid salt crosslinked products, and partially crosslinked water-swellable polymers such as polyethylene oxide and polyacrylamide. Among these, acrylic acid-based or acrylate-based components, which are excellent in the water absorption amount and the water absorption rate, are suitable. In the production process of the water-absorbent polymer having the water-absorbing performance, it is possible to adjust the water absorbing force and the water absorbing speed by adjusting the crosslinking density and the crosslinking density gradient. When the blending amount of the water-absorbent polymer is increased because of the necessity of promoting the permeation to the absorbent body 4 side by the middle-high portion 6, a so-called gel blocking phenomenon occurs, so it is preferable that the water-absorbent polymer be blended at a ratio of 1% to 10% in terms of weight relative to the total weight of the pulp fiber and the synthetic fiber. Note that when the content of the water-absorbent polymer exceeds 50%, entanglement between the pulp fibers is eliminated, and the sheet strength decreases, and, therefore, breakage and cracking, etc., are liable to occur, which is undesirable.

Figure 3:
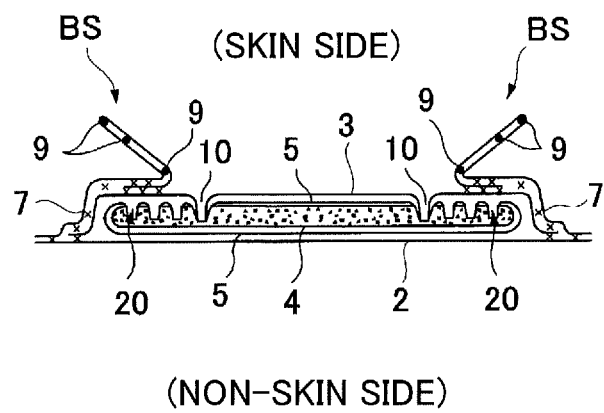
FIG. 3 is a view taken along an arrow line of FIG. 1.
Figure 4:
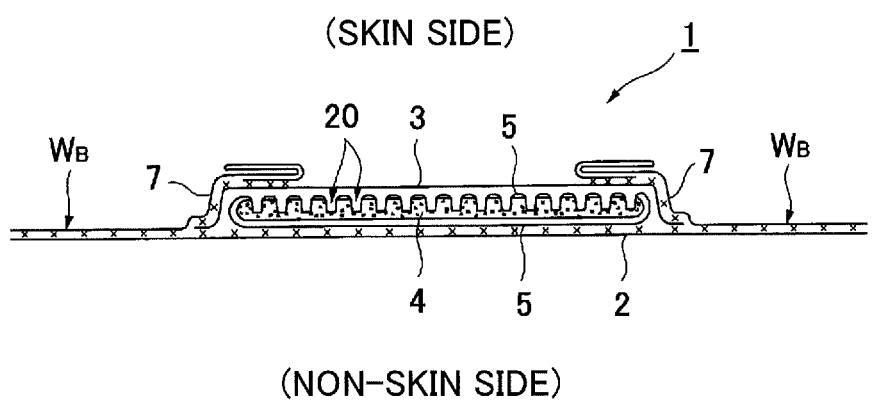
FIG. 4 is a view taken along an arrow line IV-IV of FIG. 1.

In the illustrated example, the width dimension of the liquid permeable surface sheet 3 is slightly longer than the width of the absorbent body 4 as illustrated in the cross sectional views of FIGS. 2 to 4, and only covers the absorbent body 4, and at the outer sides thereof, the side non-woven fabric 7 separate from the liquid permeable surface sheet 3 is disposed. The side non-woven fabric 7 is formed by using a non-woven fabric that has undergone appropriate water repellent treatment or hydrophilic treatment, according to the purpose, such as preventing menstrual blood and vaginal discharge, etc., from penetrating, or enhancing the touching feeling on the skin, etc. The side non-woven fabric 7 may be formed of a material such as natural fiber, synthetic fiber, and regenerated fiber, etc., by an appropriate processing method; however, in order to eliminate the sense of roughness and to prevent steaming, it is preferable to use non-woven fabric having reduced fabric weight and having air permeability. Specifically, it is desirable to use non-woven fabric fabricated to have a fabric weight of 13 g/m$^2$ to 23 g/m$^2$, and in order to reliably prevent the permeation of body fluids, water repellent treated non-woven fabric coated with a silicon-based, paraffin-based, or alkyl chromic chloride-based water repellent, etc., is suitably used.

As illustrated in FIGS. 2 to 4, the side non-woven fabric 7 has a structure in which the outer portion of the side non-woven fabric 7 from the widthwise intermediate portion, is adhered, by an adhesive such as hot melt, to a range extending from a predetermined inner position to the outer edge of the liquid impermeable back sheet 2, so that a flap portion in which the absorbent body 4 does not intervene, is formed on both side portions of the absorbent body 4, by the laminated sheet portion of the side non-woven fabric 7 and the liquid impermeable back sheet 2. By this flap portion, a pair of right and left wing-shaped flaps W, W is formed at positions of the absorbent body side portions substantially corresponding to the body fluid excretion part H, and hip-holding flaps $W_B$, $W_B$ can be formed at positions on the buttock side (rear side) thereof. An adhesive layer (not illustrated) is provided on the outer surface side of the wing-shaped flaps W, W and the hip-holding flaps $W_B$, $W_B$, respectively. When attaching the sanitary napkin 1 to shorts, the wing-shaped flaps W, W are folded back to the opposite side at the positions of fold lines RL of the base end part, and wrapped around the crotch part of the shorts to be fastened, and the hip-holding flaps $W_B$, $W_B$ are fastened to the inner face of the shorts.

On the other hand, the inner side portion of the side non-woven fabric 7 is folded back to be almost two-fold, and inside this double sheet portion, one or more, or three in the illustrated example, threadlike elastically extensible members 9, 9 . . . are disposed in a state where both ends or appropriate positions in the longitudinal direction are fixed to the intermediate portion in the height direction of the side non-woven fabric 7. As illustrated in FIG. 4, at the front and rear end portions, the double sheet portion is adhered to the absorbent body 4 side in a state where the side non-woven fabric 7 is folded once outside to be laminated, whereby as illustrated in FIG. 2, linear standing gathers BS, BS standing on the surface side while tilting toward the outside are formed as a pair on the right and left sides.

[Compressed Parts]

Figure 5:
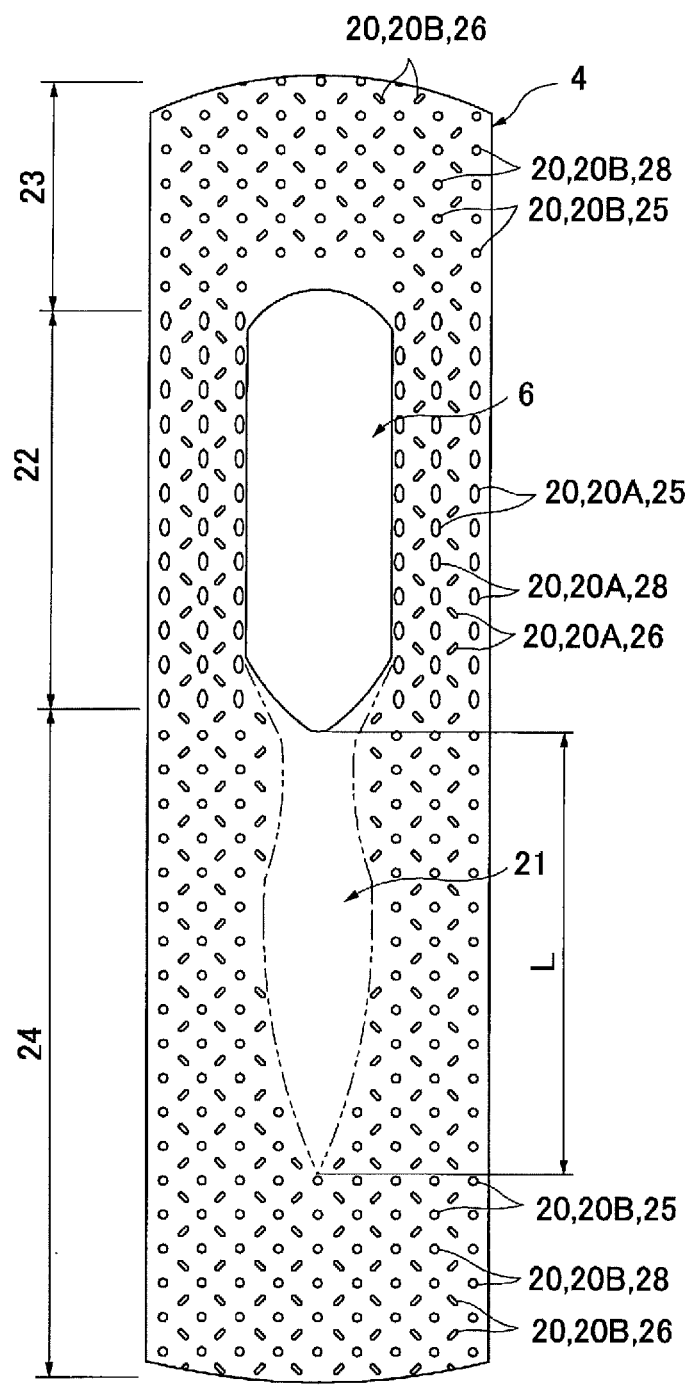
FIG. 5 is a plan view of an absorbent body 4.

In the present sanitary napkin 1, as illustrated in FIG. 5, in the absorbent body 4, multiple compressed parts 20, 20, . . . are formed in a region other than the region that is a widthwise center portion extending along the longitudinal direction, the region that is the widthwise center portion including the portions corresponding to the body fluid excretion part H and the intergluteal cleft of the wearer; and in the region that is the widthwise center portion, a region including the portion corresponding to the intergluteal cleft where the compressed parts 20 are not formed, is the easily deformable region 21. That is, the region including the portion corresponding to the body fluid excretion part H of the wearer, and the region (the easily deformable region 21) including the portion corresponding to the intergluteal cleft continuing to the rear side, are non-compressed regions in which the compressed parts 20 are not formed, and the multiple compressed parts 20, 20, . . . are formed in the outer peripheral portion of the absorbent body 4 so as to surround the non-compressed regions. The region including the portion corresponding to the body fluid excretion part H is a widthwise center region including all portions where the body fluid excretion part H of the wearer contacts when the sanitary napkin 1 is worn, and the range of this region in the longitudinal direction of the napkin substantially corresponds to the longitudinal range of wing-shaped flaps W, in the case where the wing-shaped flaps W are provided on both sides. Furthermore, the region including the portion corresponding to the intergluteal cleft is a widthwise center region including at least a part of the intergluteal cleft of the wearer when the sanitary napkin 1 is worn, and is a range extending rearward from the start position of the intergluteal cleft on the crotch side to a middle position of the intergluteal cleft.

The compressed parts 20 are formed by hot embossing to compress the absorbent body 4 to a depth within the range of the thickness of the absorbent body 4, from the skin side to the non-skin side of the absorbent body 4, and the compressed parts 20 are formed by compressing only the absorbent body 4 or by integrally compressing the encapsulating sheet 5 and the absorbent body 4 from the skin side of the absorbent body 4 surrounded by the encapsulating sheet 5. Note that in the illustrated example, the compressed parts 20 are formed by compressing the absorbent body 4 from the skin side toward the non-skin side; however, the absorbent body 4 may be compressed from the non-skin side to the skin side. In order to apply the compressed parts 20, 20, . . . to the absorbent body 4, an embossing roll having multiple protruding portions on the roll surface and a flat roll having a flat surface are disposed opposite to each other, the absorbent body 4 is passed through between these rolls, so that the compressed parts 20, 20, . . . are continuously applied on the absorbent body. At this time, both the embossing roll and the flat roll may be heated, or only the embossing roll may be heated.

The easily deformable region 21 is a region provided in the region including the portion corresponding to the intergluteal cleft of the wearer and in which the compressed parts 20 are not formed. Therefore, the rigidity of the easily deformable region 21 is relatively lower than that of the region where the compressed parts 20 are formed, and the easily deformable region 21 is a region where the absorbent body is easily deformed due to contours of the body and movements of the body. When the absorbent body 4 having a low fabric weight is used, deformation is more likely to occur. Most of the periphery of the easily deformable region 21, except for the portion corresponding to the body fluid excretion part H on the front side, is a region in which the rigidity is enhanced by the compressed parts 20, and, therefore, it is possible to prevent splitting, etc., of the absorbent body 4 in the easily deformable region 21.

It is preferable to provide the middle-high portion 6 of the absorbent body thickened toward the skin side, in a region including the portion corresponding to the body fluid excretion part H of the wearer, where the compressed parts 20 are not formed, similar to the easily deformable region 21. Accordingly, the adhesion with the body fluid excretion part H is improved, the amount of body fluid that leaks out is greatly reduced, and the region corresponding to the body fluid excretion part H is reinforced by the middle-high portion 6, and, therefore, it is possible to prevent the twisting and splitting of the absorbent body 4 in this region.

In the present sanitary napkin 1 having the above-described configuration, by forming multiple compressed parts 20, 20, . . . in regions other than a predetermined region of the absorbent body 4, the rigidity of the absorbent body 4 in the region to which the compressed parts 20 are applied is increased, so that even when the absorbent body 4 having a low fabric weight is used, it is possible to prevent twisting and splitting of the absorbent body 4 caused by the movement of the body while wearing the sanitary napkin 1. On the other hand, the region including the portion corresponding to the intergluteal cleft of the wearer is the easily deformable region 21 in which the compressed parts 20 are not formed, and, therefore, the widthwise center portion is likely to deform by protruding toward the skin side in the longitudinal direction along the intergluteal cleft when the sanitary napkin 1 is worn, and it is possible to maintain the capability of fitting onto the buttocks.

In order to confirm this effect, a water absorption test using a dummy figure was carried out. As a result, in the case where the compressed parts 20 . . . were not provided, when the fabric weight of the absorbent body was low (absorbent body fabric weight: 290 g/m$^2$ to 410 g/m$^2$), the rigidity of the absorbent body was low, and, therefore, the absorbent body 4 was easily twisted due to leg pressure, and leakage easily occurred. On the other hand, in the case of the present sanitary napkin 1 provided with the compressed parts 20, even if the fabric weight of the absorbent body 4 was low (absorbent body fabric weight: 290 g/m² to 410 g/m²), the rigidity of the outer edge portions was enhanced by the compressed parts 20 . . . , and, therefore, even if leg pressure is applied, the absorbent body 4 was less likely to twist, and leakage was less likely to occur. On the other hand, for the purpose of enhancing the rigidity of the absorbent body without providing the compressed parts 20 . . . , when the fabric weight of the absorbent body was increased in a region (absorbent body fabric weight in this region being 415 g/m² to 500 g/m²) other than the region that is the widthwise center portion extending along the longitudinal direction including the portions corresponding to the body fluid excretion part H and the intergluteal cleft, the suppleness of the absorbent body was eliminated, such that the absorbent body did not follow the body of the wearer and could not come in close contact with the skin surface, and, therefore, the body fluid was easily transmitted along the skin surface to leak outside.

As illustrated in FIG. 5, the easily deformable region 21 is preferably formed to extend rearward from the rear end of the region including the portion corresponding to the body fluid excretion part H of the wearer (the portion where the middle-high portion 6 is disposed) to an intermediate position in the longitudinal direction of the absorbent body 4. That is, it is preferable that the easily deformable region 21 is not formed up to the rear end of the absorbent body 4, but to the intermediate position in the longitudinal direction of the absorbent body 4. Accordingly, the rear end portion of the absorbent body 4 on the rear side of the easily deformable region 21 is made highly rigid by the compressed parts 20, 20, . . . , so that twisting and splitting of the absorbent body 4 in the easily deformable region 21 can be reliably prevented.

The length L of the easily deformable region 21 extending rearward from the rear end of the middle-high portion 6 is preferably 90 mm to 110 mm, particularly 100 mm to 105 mm. Accordingly, the easily deformable region 21 is formed over a predetermined length range from the vicinity of the starting position of the intergluteal cleft of the crotch to a predetermined rear position, so that the absorbent body 4 fits the intergluteal cleft, and the body fluid is less likely to flow from the body fluid excretion part H to the intergluteal cleft, so that rear leakage can be reliably prevented.

It is preferable that the planar shape of the easily deformable region 21 is formed to be slightly narrower than the middle-high portion 6, and the rear end portion of the easily deformable region 21 is tapered rearward. Furthermore, it is also preferable to provide a narrowed portion in the width direction near the rear end of the middle-high portion 6. The narrowed portion in the width direction is formed so that the easily deformable region 21 deforms to protrude toward the skin side in a narrow and long manner in the longitudinal direction of the napkin when pressure from the outside in the width direction is applied, so as to facilitate the fitting into the long, narrow, and fine depression extending from the perineum portion to the buttocks start position of the crotch of the wearer. Accordingly, it is possible to reliably prevent the flow of the bodily fluid that is transmitted rearward from the body fluid excretion part H along the skin.

The compressed parts 20 may be provided by the same pattern throughout the entire absorbent body 4; however, it is preferable that the ratio of the area occupied by the compressed parts 20 per unit area of the absorbent body 4, is higher for the compressed parts 20A applied to the regions (both side regions 22, 22) on both sides of the portion corresponding to the body fluid excretion part H, than for compressed parts 20B applied to the region (front region 23) on the front side of the portion corresponding to the body fluid excretion part H and the region (rear region 24) on the rear side of the portion corresponding to the body fluid excretion part H. Here, the area of the compressed parts 20 is the area of the bottom surface of the compressed parts 20. By providing the compressed parts 20A in the both side regions 22 to have a relatively large area, the rigidity of the absorbent body 4 in the both side regions 22 is increased, and twisting and splitting of the absorbent body 4 caused by the leg pressure from the outside in the width direction can be reliably prevented. The ratio of the area occupied by the compressed parts 20 per unit area of the absorbent body 4 is preferably approximately 10% to 20% in the both side regions 22, and preferably approximately 5% to 10% in the front region 23 and the rear region 24.

Furthermore, as a preferable compression part pattern for preventing twisting and splitting of the absorbent body 4, as illustrated in FIG. 5, it is preferable to dispose oval compressed parts 26, 26 . . . adjacent to each other in a cross direction centering around a dot-like compressed part 25, and repeatedly form this pattern in a substantially rhombic grid, and to dispose one dot-like compressed part 28 at the center of each rhombic grid mesh 27. By forming such a compressed part pattern, the restoring force of the absorbent body 4 after applying the compressed parts 20 is appropriately suppressed, and the increase in rigidity of the absorbent body 4 due to the application of the compressed parts 20 is ensured. Furthermore, by disposing the dot-like compressed parts 25 and the oval compressed parts 26 in a substantially rhombic grid pattern, the leg pressure from the outer side in the width direction can be received while the leg pressure is distributed in the longitudinal direction by the inclined oval compressed parts 26, and it is possible to prevent twisting and splitting of the absorbent body caused by the concentration of pressure in a specific direction. In the illustrated example, the dot-like compressed part 25 disposed at the corner of each rhombic grid mesh 27, and the dot-like compressed part 28 disposed at the center of each rhombic grid mesh 27 have the same shape; however, the dot-like compressed part 25 and the dot-like compressed part 28 may have different shapes.

Figure 6:
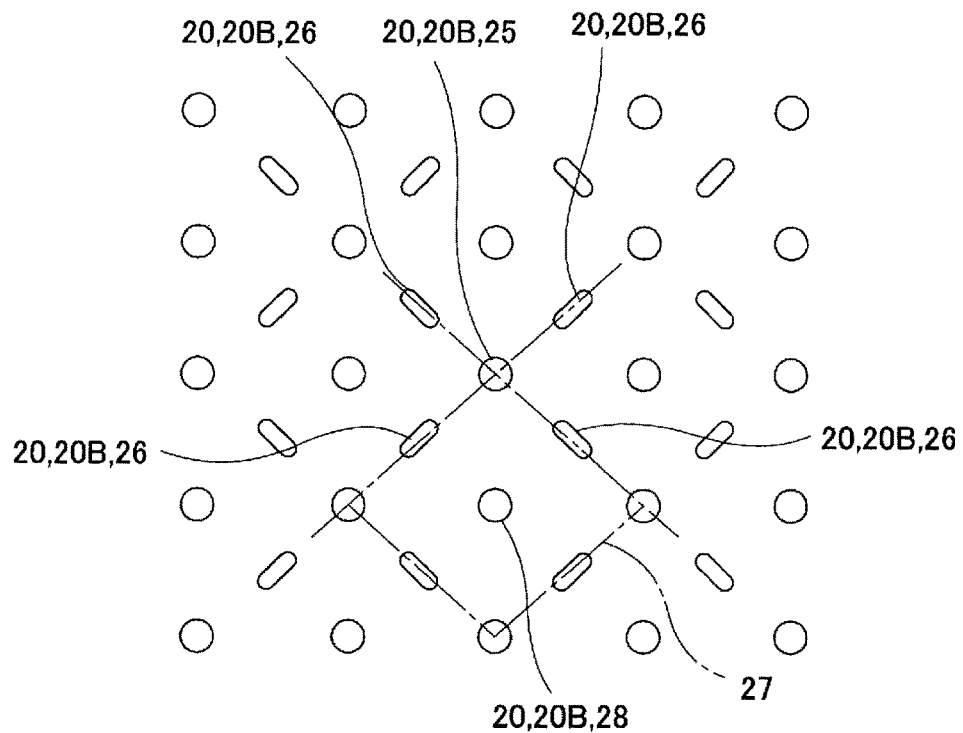
FIG. 6 is an enlarged view of a compressed part pattern in a front region 23 and a rear region 24 of a portion corresponding to a body fluid excretion part.
Figure 7:
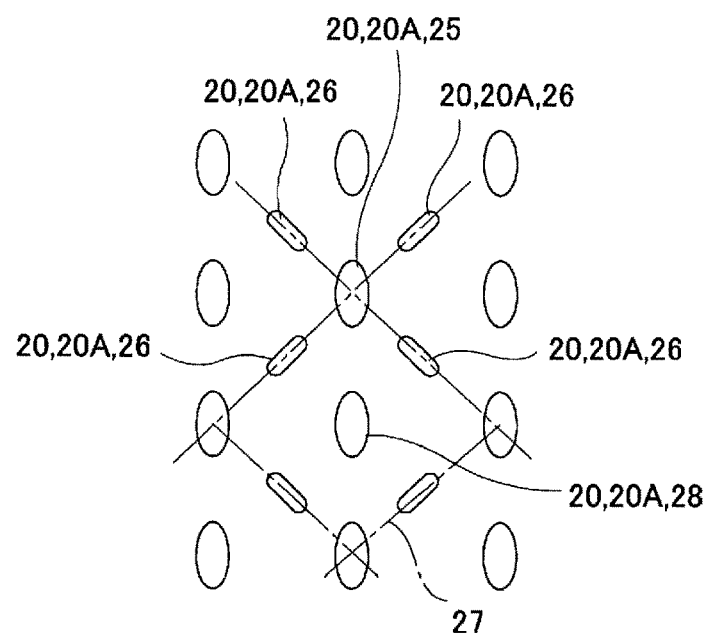
FIG. 7 is an enlarged view of a compressed part pattern in both side regions 22 of a portion corresponding to a body fluid excretion part.

As illustrated in FIG. 6, it is preferable that the dot-like compressed parts 25, 28 formed in the front region 23 and the rear region 24 are respectively formed to have a substantially circular shape, and as illustrated in FIG. 7, it is preferable that the dot-like compressed parts 25, 28 formed in the both side regions 22, 22 have a relatively large area as compared with the dot-like compressed parts 25, 28 formed in the front region 23 and the rear region 24, and are formed to have a long substantially oval shape in the longitudinal direction of the napkin. That is, without changing the area of the oval compressed parts 26, the ratio of the area occupied by the compressed parts 20 per unit area of the absorbent body 4 is higher for the compressed parts 20A in the both side regions 22 than for the compressed parts 20B in the front region 23 and the rear region 24. Accordingly, in the both side regions 22, a line having high rigidity along the longitudinal direction of the napkin is formed by the dot-like compressed parts 25, 28 formed to have a long oval shape in the longitudinal direction of the napkin, so that the resistance force against the leg pressure from the outside in the width direction can be increased.

In the both side regions 22, the size of the dot-like compressed parts 25, 28, having an oval shape, is preferably 3 mm to 6 mm, particularly 3 mm to 5 mm in the longitudinal direction, and 1 mm to 5 mm, particularly 2 mm to 3 mm in the short direction. The size of the oval compressed parts 26 is preferably 1.5 mm to 7.5 mm, particularly 2 mm to 4 mm in the longitudinal direction, and 0.5 mm to 3 mm, particularly 0.5 mm to 1.5 mm in the short direction. Furthermore, in the front region 23 and the rear region 24, the size of the dot-like compressed parts 25, 28 having a circular shape, is preferably a diameter of approximately 1 mm to 6 mm, particularly 1 mm to 3 mm, and the size of the oval compressed parts 26 is preferably 1 mm to 6 mm, particularly 2 mm to 3.5 mm in longitudinal direction, and 0.5 mm to 3 mm, particularly 0.5 mm to 1.5 mm in the short direction. The minimum separation distance between the dot-like compressed parts 25, 28 and the oval compressed parts 26 is set to be smaller in the both side regions 22 than in the front region 23 and the rear region 24, specifically preferably 1.5 mm to 3 mm in the both side regions 22, and 2 mm to 4 mm in the front region 23 and the rear region 24.

The present sanitary napkin 1 has a compressed part pattern that is a combination of the dot-like compressed parts 25, 28 and the oval compressed parts 26. However, if the sanitary napkin 1 has a rhombic grid pattern formed only by the oval compressed parts 26 without the dot-like compressed parts 25, 28, the spacing between the compressed parts becomes too wide and the area of the uncompressed parts increases, so in the case of an absorbent body having a high fabric weight, the compressive strength is weakened by the restoring force of the absorbent body, and desired rigidity may not be obtained in some cases. Furthermore, if the length of the oval compressed parts is made longer or the mesh size of the rhombic grid is made finer in order to reduce the area of the uncompressed parts, the hardness of the oval compressed parts will be felt strongly at the time of wearing the napkin, and the wearing feeling is degraded.

REFERENCE SIGNS LIST

1 ... sanitary napkin, 2 ... liquid impermeable back sheet, 3 ... liquid permeable surface sheet, 4 ... absorbent body, 5 ... encapsulating sheet, 6 ... middle-high portion, 7 ... side non-woven fabric, 8 ... compressed groove, 9 ... threadlike elastically extensible members, 20 ... compressed parts, 21 ... easily deformable region, 22 ... both side regions, 23 ... front region, 24 ... rear region, 25, 28 ... dot-like compressed part, 26 ... oval compressed part, 27 ... rhombic grid mesh

The invention claimed is:

1. An absorbent article in which an absorbent body is interposed between a liquid permeable surface sheet and a liquid impermeable back sheet, wherein
   in the absorbent body, multiple compressed parts are formed in a region other than a region that is a widthwise center portion extending along a longitudinal direction, the region that is the widthwise center portion including a portion corresponding to a body fluid excretion part of a wearer and a portion corresponding to an intergluteal cleft of the wearer, and
   a region including the portion corresponding to the intergluteal cleft is an easily deformable region where the compressed parts are not formed, and
wherein a ratio of an area occupied by the compressed parts per unit area of the absorbent body is higher for the compressed parts that are formed in regions on both sides of the portion corresponding to the body fluid excretion part, than for the compressed parts that are formed in a region on a front side of and in a region on a rear side of the portion corresponding to the body fluid excretion part.

2. The absorbent article according to claim 1, wherein the easily deformable region extends to an intermediate position in the longitudinal direction of the absorbent body and does not reach a rear end of the absorbent body, and the compressed parts are formed in a range extending behind the easily deformable region to the rear end of the absorbent body.

3. The absorbent article according to claim 1, wherein a middle-high portion with an increased thickness of the absorbent body toward a skin side is provided in the absorbent body in the region including the portion corresponding to the body fluid excretion part.

4. An absorbent article in which an absorbent body is interposed between a liquid permeable surface sheet and a liquid impermeable back sheet, wherein
   in the absorbent body, multiple compressed parts are formed in a region other than a region that is a widthwise center portion extending along a longitudinal direction, the region that is the widthwise center portion including a portion corresponding to a body fluid excretion part of a wearer and a portion corresponding to an intergluteal cleft of the wearer, and
   a region including the portion corresponding to the intergluteal cleft is an easily deformable region where the compressed parts are not formed, wherein
   the compressed parts are formed in a compressed part pattern forming a substantially rhombic grid, in which a pattern, in which oval compressed parts are disposed adjacent to each other in a cross direction centering around a dot compressed part, is repeated, and
   the dot compressed part is disposed at a center of each mesh of the rhombic grid.

5. The absorbent article according to claim 4, wherein
   the dot compressed part, which is formed in a region on a front side of and in a region on a rear side of the portion corresponding to the body fluid excretion part, is formed such that a length in the longitudinal direction of the absorbent article and a length in a width direction of the absorbent article are substantially a same length, and
   the dot compressed part, which is formed in regions on both sides of the portion corresponding to the body fluid excretion part, is formed so as to have a shape elongated in the longitudinal direction of the absorbent article, and to have a relatively larger area than the dot compressed part formed in the region on the front side of and in the region on the rear side of the portion corresponding to the body fluid excretion part.

\* \* \* \* \*